(12) United States Patent
Leeds

(10) Patent No.: US 11,571,365 B2
(45) Date of Patent: Feb. 7, 2023

(54) INTRALUMINAL TUBES WITH DEPLOYABLE STRUCTURES AND RELATED METHODS

(71) Applicant: BAYLOR RESEARCH INSTITUTE, Dallas, TX (US)

(72) Inventor: Steven G. Leeds, Dallas, TX (US)

(73) Assignee: BAYLOR RESEARCH INSTITUTE, Dallas, TX (US)

( * ) Notice: Subject to any disclaimer, the term of this patent is extended or adjusted under 35 U.S.C. 154(b) by 0 days.

(21) Appl. No.: 15/510,161

(22) PCT Filed: Sep. 9, 2015

(86) PCT No.: PCT/US2015/049130
§ 371 (c)(1),
(2) Date: Mar. 9, 2017

(87) PCT Pub. No.: WO2016/040444
PCT Pub. Date: Mar. 17, 2016

(65) Prior Publication Data
US 2017/0296438 A1    Oct. 19, 2017

Related U.S. Application Data

(60) Provisional application No. 62/047,915, filed on Sep. 9, 2014.

(51) Int. Cl.
*A61J 15/00* (2006.01)
*A61M 1/00* (2006.01)
(Continued)

(52) U.S. Cl.
CPC ....... *A61J 15/0003* (2013.01); *A61J 15/0038* (2013.01); *A61M 1/84* (2021.05);
(Continued)

(58) Field of Classification Search
CPC .. A61M 25/04; A61M 27/00; A61M 16/0461; A61M 16/0666;
(Continued)

(56) References Cited

U.S. PATENT DOCUMENTS

| 88,695 A | 4/1869 | Davidson | 604/105 |
| 673,321 A | 4/1901 | Lincoln | 604/105 |

(Continued)

FOREIGN PATENT DOCUMENTS

| CN | 203060547 | 7/2013 |
| WO | WO 2012/109198 | 8/2012 |

OTHER PUBLICATIONS

International Search Report and Written Opinion issued in application No. PCT/US15/49130, dated Dec. 8, 2015.
(Continued)

*Primary Examiner* — Theodore J Stigell
*Assistant Examiner* — Hong-Van N Trinh
(74) *Attorney, Agent, or Firm* — Norton Rose Fulbright US LLP

(57) ABSTRACT

This disclosure includes intraluminal tubes comprising: an elongated tube (e.g., having a proximal portion, a distal portion configured to be disposed inside of an internal cavity of a patient, and a sidewall defining a lumen extending from the proximal portion to the distal portion, the distal portion defining one or more openings in fluid communication with the lumen) and a plurality of deployable tines, each coupled to the tube and disposed outside the sidewall of the distal portion, where each tine is movable from a collapsed state to a deployed state in which a portion of the tine extends laterally away from the distal portion of the tube. In some of the present intraluminal tubes, the sidewall of the distal portion defines a plurality of longitudinal grooves, and each
(Continued)

tine is disposed in a different one of the grooves when the tines are in the collapsed state.

18 Claims, 6 Drawing Sheets

(51) Int. Cl.
*A61M 25/04* (2006.01)
*A61M 25/00* (2006.01)

(52) U.S. Cl.
CPC ....... *A61M 25/007* (2013.01); *A61M 25/0074* (2013.01); *A61M 25/04* (2013.01); *A61M 2210/1053* (2013.01)

(58) Field of Classification Search
CPC ........ A61M 2025/0079; A61M 25/007; A61M 3/0291; A61M 2025/0213; A61M 29/00; A61M 29/02; A61M 2029/025; A61M 3/0295; A61M 1/84; A61M 25/0074; A61M 2210/1053; A61J 15/0003; A61J 15/0034; A61J 15/003–15/0038; A61B 5/6858; A61B 5/6859; A61B 17/221; A61B 17/320725
See application file for complete search history.

(56) References Cited

U.S. PATENT DOCUMENTS

| | | | | |
|---|---|---|---|---|
| 716,240 A | * | 12/1902 | Jones | A61M 3/0291 |
| | | | | 604/107 |
| 827,193 A | * | 7/1906 | George | A61M 25/04 |
| | | | | 604/105 |
| 1,115,224 A | * | 10/1914 | McAllum | A61M 25/1018 |
| | | | | 604/98.02 |
| 1,155,169 A | | 9/1915 | Starkweather | 604/105 |
| 1,338,464 A | * | 4/1920 | Shafer | A61M 3/0279 |
| | | | | 604/279 |
| 2,072,346 A | | 3/1937 | Smith | 27/24.2 |
| 3,065,750 A | * | 11/1962 | Mandell | A61M 3/0295 |
| | | | | 604/84 |
| 3,108,595 A | * | 10/1963 | Overment | A61M 25/04 |
| | | | | 604/105 |
| 3,966,938 A | | 6/1976 | Ott et al. | 514/292 |
| 4,043,322 A | * | 8/1977 | Robinson | A61B 1/303 |
| | | | | 600/571 |
| 4,180,076 A | | 12/1979 | Betancourt | 604/101.03 |
| 4,634,435 A | | 1/1987 | Ingraham | 604/268 |
| 4,650,466 A | | 3/1987 | Luther | 604/95.04 |
| 4,834,724 A | | 5/1989 | Geiss et al. | 604/540 |
| 4,921,484 A | | 5/1990 | Hillstead | 604/104 |
| 5,135,517 A | | 8/1992 | McCoy | |
| 5,273,529 A | | 12/1993 | Idowu | 604/500 |
| 5,643,230 A | * | 7/1997 | Linder | A61M 25/0068 |
| | | | | 604/264 |
| 5,690,620 A | | 11/1997 | Knott | 604/516 |
| 5,840,067 A | | 11/1998 | Berguer et al. | 604/104 |
| 6,942,641 B2 | | 9/2005 | Seddon | 604/107 |
| 8,529,443 B2 | | 9/2013 | Maloney | 600/201 |
| 9,597,108 B2 | * | 3/2017 | Ahn | A61B 17/320725 |
| 2003/0167069 A1 | | 9/2003 | Gonzales et al. | 606/200 |
| 2003/0209258 A1 | | 11/2003 | Morejon | 134/16 |
| 2005/0165357 A1 | | 7/2005 | McGuckin et al. | 604/171 |
| 2007/0225651 A1 | | 9/2007 | Rosenberg et al. | 604/174 |
| 2008/0109069 A1 | | 5/2008 | Coleman et al. | 623/1.25 |
| 2009/0062771 A1 | | 3/2009 | Tarola et al. | 604/516 |
| 2009/0240278 A1 | | 9/2009 | Deutsch | 606/198 |
| 2011/0034936 A1 | | 2/2011 | Maloney | 606/108 |
| 2013/0123708 A1 | | 5/2013 | Sellers et al. | 604/177 |

OTHER PUBLICATIONS

Supplementary European Search Report Issued in European Application No. EP15840441.8, dated Apr. 4, 2018.

* cited by examiner

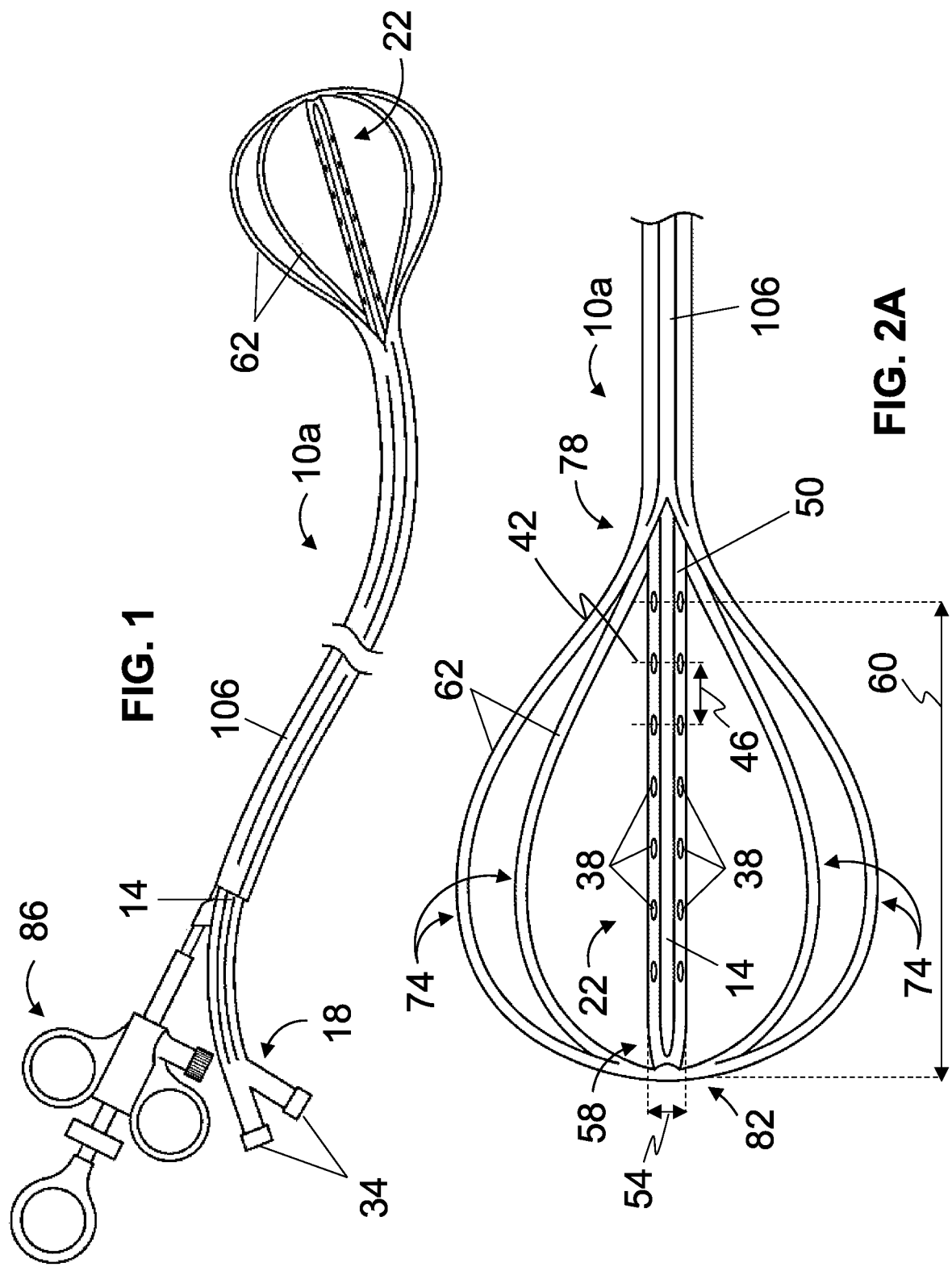

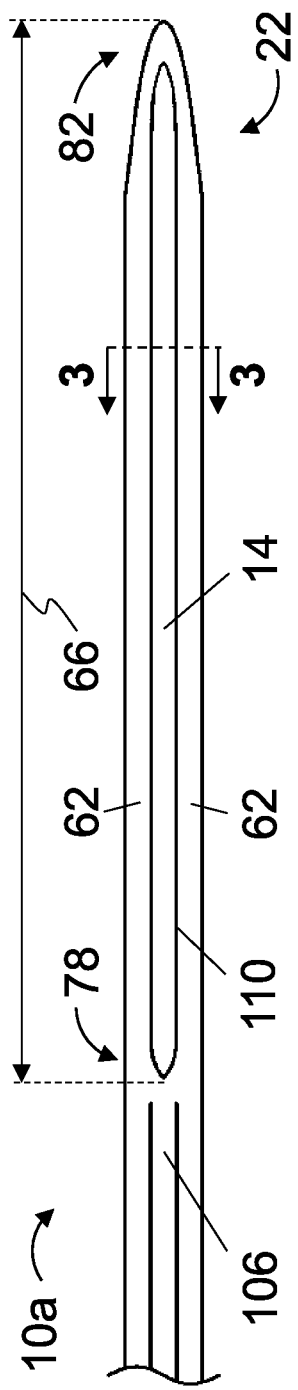
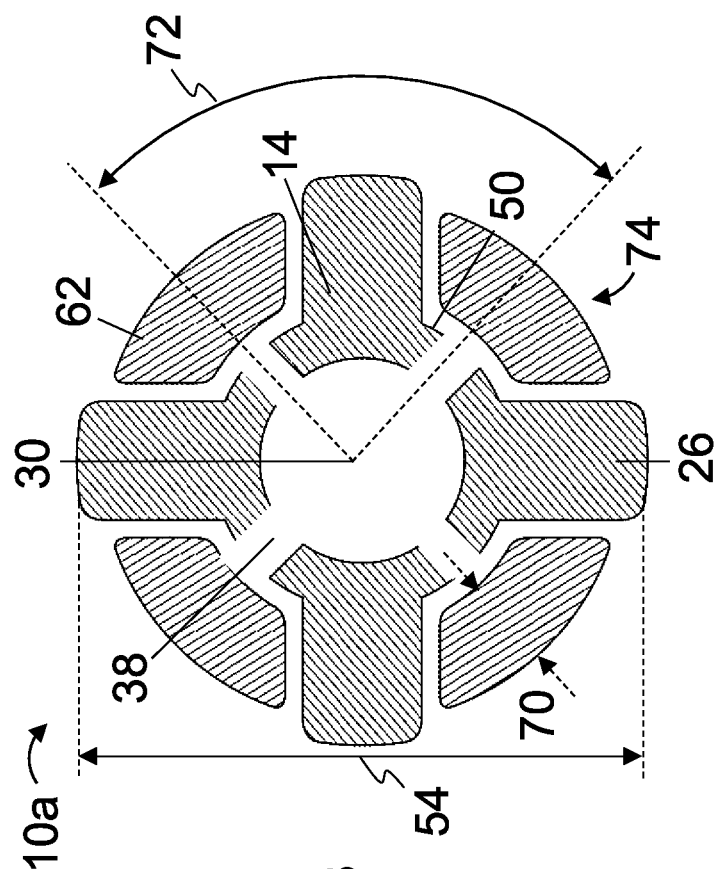

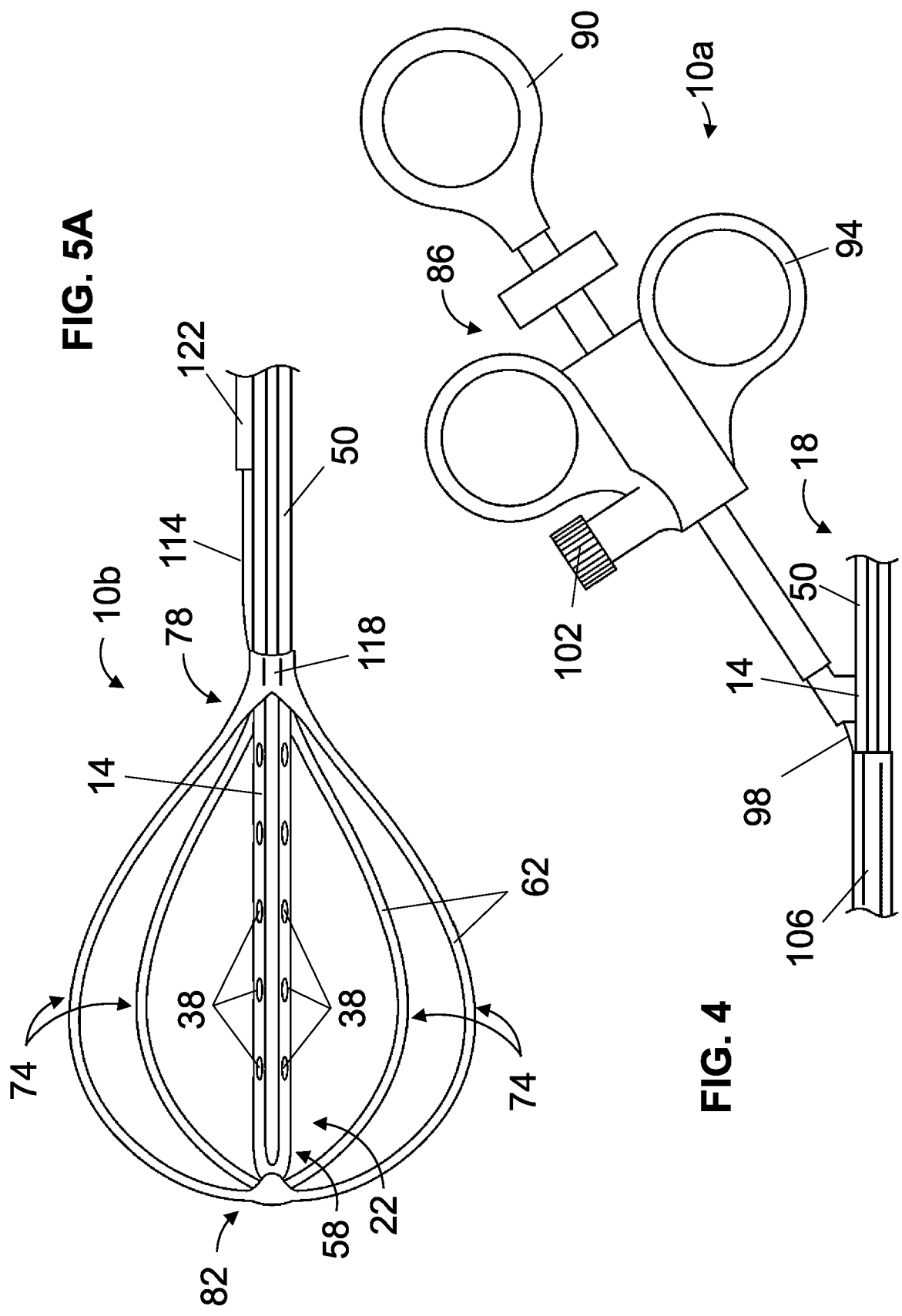

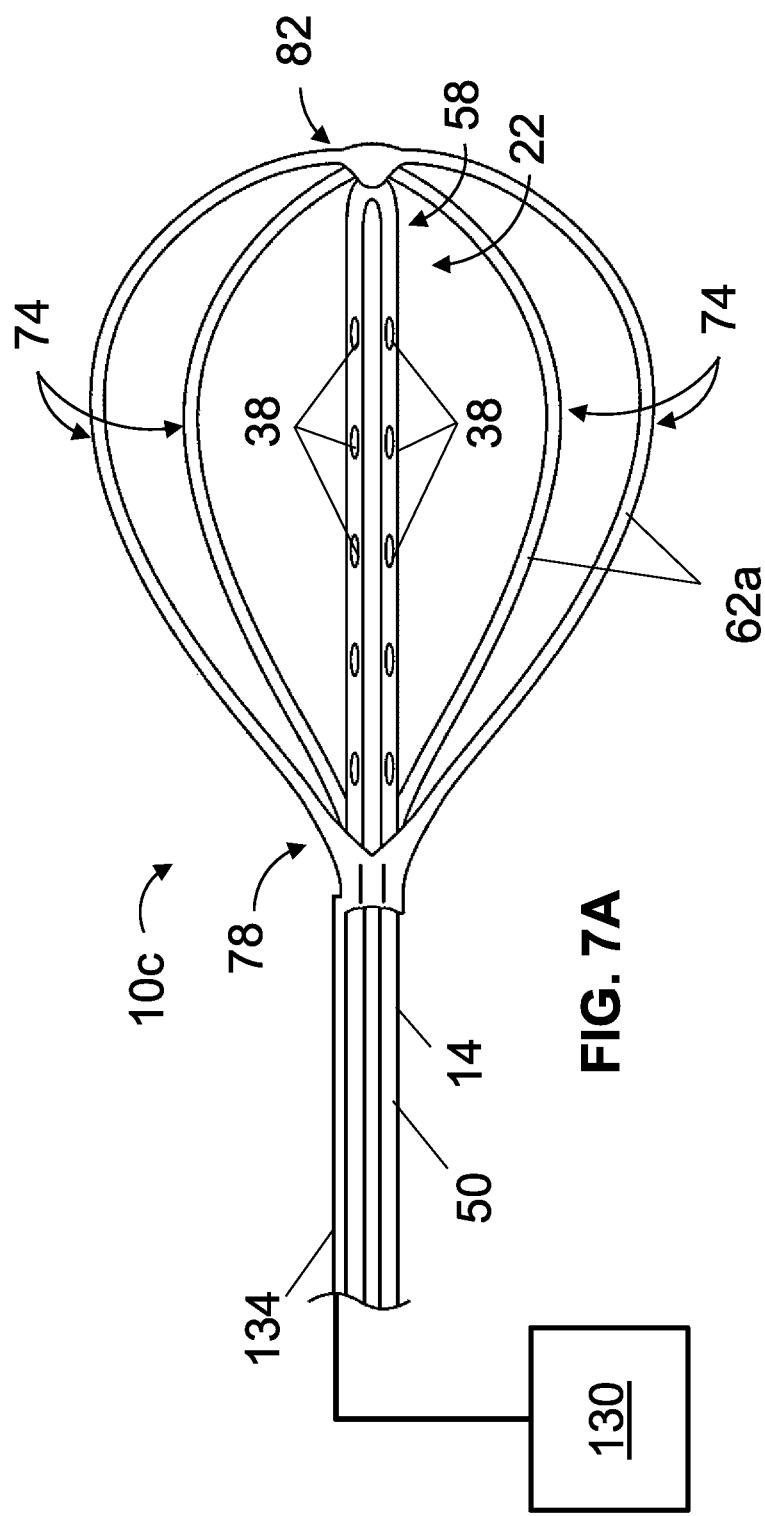
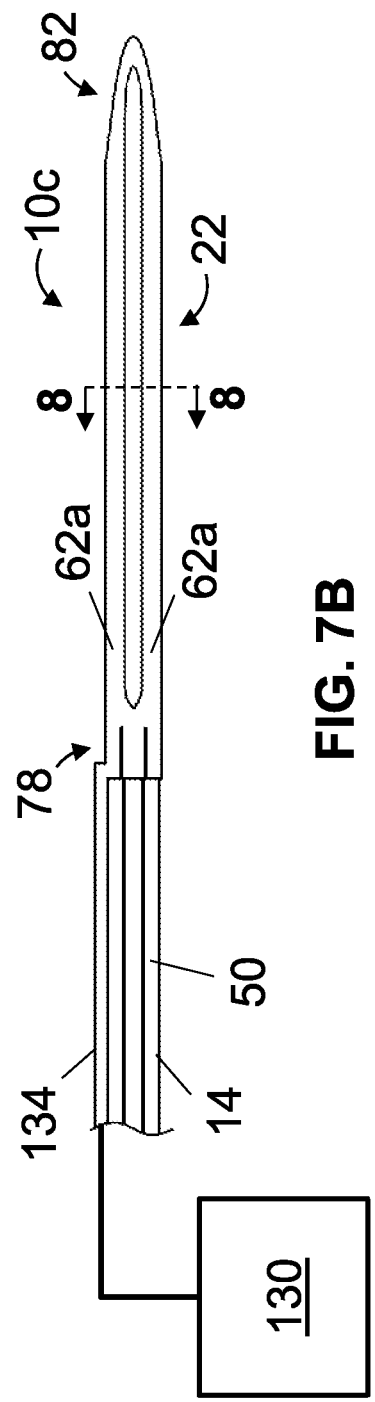
FIG. 7A
FIG. 7B

INTRALUMINAL TUBES WITH DEPLOYABLE STRUCTURES AND RELATED METHODS

CROSS-REFERENCES TO RELATED APPLICATIONS

This application is a national phase under 35 U.S.C. § 371 of International Application No. PCT/US2015/049130, filed Sep. 9, 2015, which claims priority to U.S. Provisional Patent Application No. 62/047,915, filed on Sep. 9, 2014 and entitled "INTRALUMINAL TUBES WITH DEPLOYABLE STRUCTURES AND RELATED METHODS," the entire contents of each of which are incorporated by reference in their entirety.

BACKGROUND

1. Field of Invention

The present invention relates generally to intubation, and more specifically, but not by way of limitation, to intraluminal tubes.

2. Description of Related Art

Intraluminal tubes are typically used to communicate fluids to and/or from an internal cavity of a patient, such as, for example, a patient's stomach, colon, bladder, heart, vein, artery, other internal cavity and/or passageway, and/or the like. Such fluids can include, but are not limited to, liquids (e.g., water, body fluids, and/or the like), gasses (e.g., air, and/or the like), and/or suspended solids and/or particulate matter (e.g., food, medications, and/or the like).

Examples of intraluminal tubes include, but are not limited to, nasogastric tubes (NGTs), abscess draining tubes, rectal tubes, urinary draining catheters, endovascular catheters, ascites drainage catheters, tubes configured to receive imaging equipment, and/or the like. In the following description, NGTs and/or nasogastric intubation are referenced by way of example to illustrate some of the common issues associated with the use of many, if not all, types of intraluminal tubes.

For example, negative pressure (e.g., suction) can be applied to a patient's stomach via an NGT to remove contents (e.g., fluids) from the patient's stomach. Stomach suction with an NGT can be an important aspect of medical and/or surgical care of patients. For example, stomach suction can be used to alleviate a distended stomach, which may predispose a patient to nausea and/or vomiting. Stomach suction can also be beneficial when, for example, a patient is undergoing a planned surgery (e.g., or is pre- or post-operative), admitted to the hospital and/or intensive care unit (ICU), taking certain medications, and/or the like.

Proper function of an NGT can be important to patient care, but maintaining such proper function can present difficulties. In some instances (e.g., particularly when suction is applied through the NGT), the tube can become occluded by stomach contents and/or portions of the stomach itself, such as the stomach mucosa. If the tube becomes occluded, suction of stomach contents and/or flow of fluids into the stomach can be impaired or halted completely.

As a result, the use of NGTs often requires frequent attention from medical personnel (e.g., nurses, doctors, and/or the like) to maintain and/or monitor for proper functioning. For example, NGTs may require manipulations, such as, for example, repositioning the NGT and/or interrupting flow (e.g., suction) through the NGT (e.g., to relieve any occlusions). If the NGT is not properly maintained and/or monitored, the beneficial treatment to the patient may be interrupted.

Current NGTs may include a channel or lumen in communication with an air blow-off port that can apply positive pressure to the patient's stomach to mitigate occlusions. However, such NGTs may introduce air into the stomach during blow-off port operation, which may be undesirable, and occlusion may reoccur once blow-off port operation ceases.

Examples of intraluminal tubes are disclosed in U.S. Pat. Nos. (1) U.S. Pat. No. 4,634,435; (2) U.S. Pat. No. 4,180,076; and (3) U.S. Pat. No. 6,942,641.

SUMMARY

By way of example, the present intraluminal tubes may be described in the context of nasogastric intubation (e.g., as NGTs); however, the present intraluminal tubes can be configured as, for example, abscess draining tubes, rectal tubes, urinary draining catheters, endovascular catheters, and/or the like.

Some embodiments of the present intraluminal tubes are configured, through a plurality of deployable tines, each coupled to and disposed outside of a sidewall of a distal portion of an elongated tube, to prevent (e.g., mucosal) occlusion of the tube (e.g., during suction) (e.g., when the tines are deployed).

Some embodiments are configured, through a plurality of longitudinal grooves defined by the sidewall of the distal portion of the elongated tube (e.g., each configured to receive a different one of the plurality of deployable tines when the tines are in a collapsed state), such that the plurality of tines each lie substantially within a cross-sectional perimeter of the tube when the tines are in the collapsed state (e.g., to minimize impact on a patient during insertion and/or removal of the intraluminal tube).

Some embodiments are configured, through a most-proximal opening(s) of the distal portion of the elongated tube (e.g., a most-proximal opening that is spaced from a tip of the tube at a distance of between 7 to 20 times a transverse dimension of the distal portion), to have a slim profile while providing for proper operation (e.g., adequate suction) (e.g., and proper operation of the slim profile intraluminal tube may be permitted and/or facilitated by occlusion prevention function of the plurality of deployable tines).

Some embodiments of the present intraluminal tubes comprise an elongated tube having a proximal portion, a distal portion configured to be disposed inside of an internal cavity of a patient, and a sidewall defining a lumen extending from the proximal portion to the distal portion, the distal portion defining one or more openings in fluid communication with the lumen, and a plurality of deployable tines, each coupled to the tube and disposed outside the sidewall of the distal portion, where each tine is movable from a collapsed state to a deployed state in which a portion of the tine extends laterally away from the distal portion of the tube.

In some embodiments, the distal portion has a transverse dimension and a tip, where a distance between the tip and the most-proximal opening(s) furthest from the tip is between 7 to 20 times the transverse dimension of the distal portion.

In some embodiments, the sidewall of the distal portion defines a plurality of longitudinal grooves. In some embodiments, the one or more openings are disposed in the plurality of grooves. In some embodiments, the plurality of deployable tines are each disposed in a different one of the grooves when the tines are in the collapsed state.

In some embodiments, the plurality of tines comprises 4 tines. In some embodiments, the plurality of tines is disposed at equiangular spaces around the distal portion of the tube. In some embodiments, the plurality of deployable tines is configured to prevent occlusion of the one or more openings when suction is applied through the lumen.

In some embodiments, a majority of each tine lies adjacent to the distal portion of the tube when the tine is in the collapsed state. In some embodiments, the portion of each tine that extends laterally away from the distal portion of the tube does not directly contact the portion of any other tine that extends laterally away from the distal portion of the tube when the tine is in the deployed state.

In some embodiments, each tine comprises a distal end and a proximal end, at least one of the distal and proximal ends coupled in fixed relation to the distal portion of the tube. In some embodiments, the distal end of each tine is coupled in fixed relation to the distal portion of the tube. In some embodiments, the proximal end of each tine is coupled in fixed relation to the distal portion of the tube.

Some embodiments comprise an operator-controlled actuator coupled to the proximal portion of the elongated tube and configured to selectively deploy or collapse the tines. In some embodiments, deployment of each tine is achieved at least in part through displacement of one end of the tine relative to an opposite end of the tine along the tube.

In some embodiments, the plurality of deployable tines each define an interior channel configured to be in fluid communication with a fluid source, the fluid source configured to cause movement of the tine between the collapsed state and the deployed state. In some embodiments, the elongated tube comprises a second lumen configured to communicate fluid between the fluid source and the interior channel of each tine.

Some embodiments comprise a flexible cable coupled to the deployable tines and configured to selectively deploy or collapse the tines, at least a portion of the cable movably disposed in the tube. In some embodiments, at least a portion of the flexible cable is disposed in the lumen. In some embodiments, the elongated tube comprises a second lumen and at least a portion of the flexible cable is disposed in the second lumen.

In some embodiments, the intraluminal tube comprises a nasogastric tube.

Some embodiments of the present methods for providing access to an internal cavity of a patient comprise inserting a distal portion of an elongated tube having a sidewall defining a lumen into the internal cavity, the distal portion defining one or more openings in fluid communication with the lumen, and deploying a plurality of deployable tines, the tines coupled to the tube and disposed outside the sidewall of the distal portion, such that a portion of each tine extends laterally away from the elongated tube to prevent occlusion of the one or more openings.

Some embodiments comprise applying suction through the elongated tube. Some embodiments comprise collapsing the plurality of deployable tines such that a majority of each tine lies adjacent the sidewall of the distal portion and removing the distal portion of the elongated tube from the internal cavity. Some embodiments comprise actuating an operator-controlled actuator coupled to a proximal portion of the elongated tube to control deployment of the tines.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, 10, and 20 percent.

Further, a device or system that is configured in a certain way is configured in at least that way, but it can also be configured in other ways than those specifically described.

The terms "comprise" (and any form of comprise, such as "comprises" and "comprising"), "have" (and any form of have, such as "has" and "having"), "include" (and any form of include, such as "includes" and "including"), and "contain" (and any form of contain, such as "contains" and "containing") are open-ended linking verbs. As a result, an apparatus that "comprises," "has," "includes," or "contains" one or more elements possesses those one or more elements, but is not limited to possessing only those elements Likewise, a method that "comprises," "has," "includes," or "contains" one or more steps possesses those one or more steps, but is not limited to possessing only those one or more steps.

Any embodiment of any of the apparatuses, systems, and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Some details associated with the embodiments described above and others are described below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The figures are drawn to scale (unless otherwise noted), meaning the sizes of the depicted elements are accurate relative to each other for at least the embodiment depicted in the figures.

FIG. 1 is a perspective view of a first embodiment of the present intraluminal tubes.

FIG. 2A is a cutaway side view of the intraluminal tube of FIG. 1, showing a plurality of deployable tines in a deployed state.

FIG. 2B is a cutaway side view of the intraluminal tube of FIG. 1, showing a plurality of deployable tines in a collapsed state.

FIG. 3 is a cross-sectional end view of the intraluminal tube of FIG. 1.

FIG. 4 is side view of an operator-controlled actuator suitable for use with the intraluminal tube of FIG. 1.

FIG. 5A is a cutaway side view of a second embodiment of the present intraluminal tubes, showing a plurality of deployable tines in a deployed state.

FIG. 7A is a cutaway side view of a third embodiment of the present intraluminal tubes, showing a plurality of deployable tines in a deployed state.

FIG. 7B is a cutaway side view of the intraluminal tube of FIG. 7A, showing a plurality of deployable tines in a collapsed state.

DETAILED DESCRIPTION OF ILLUSTRATIVE EMBODIMENTS

Figure 5B:
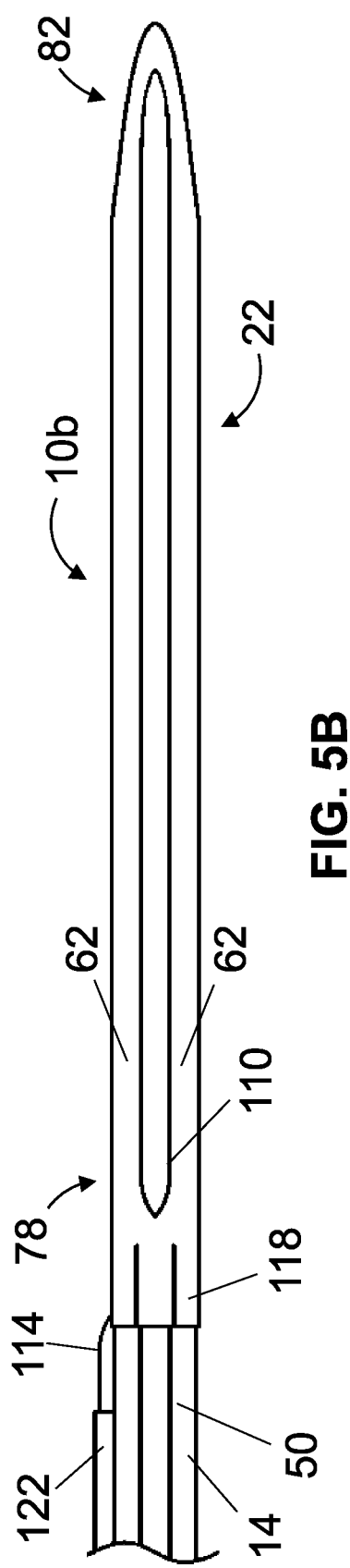
FIG. 5B is a cutaway side view of the intraluminal tube of FIG. 5A, showing a plurality of deployable tines in a collapsed state.

Referring now to the drawings, and more particularly to FIGS. 1-3, shown therein and designated by the reference numeral 10a is a first embodiment of the present intraluminal tubes. In the embodiment shown, intraluminal tube 10a comprises an elongated tube 14 (e.g., slidably coupled within a sheath 106, described in more detail below) having a proximal portion 18, a distal portion 22, and a sidewall 26 (FIG. 3) defining a lumen 30 extending from the proximal portion to the distal portion. In this embodiment, distal portion 22 is configured to be disposed inside of an internal cavity of a patient. For example, distal portion 22 of intraluminal tube 10a can be inserted into a patient's nose (with deployable tines 62 in a collapsed state, as described below), down the patient's esophagus, and into the patient's stomach (e.g., with proximal portion 18 remaining outside of the patient's body).

In the embodiment shown, proximal portion 18 defines one or more ports or fittings 34, such as, for example, Luer-type and/or any other port(s) and/or fitting(s) that can be configured to enable fluid communication between lumen 30 and a fluid and/or pressure source (e.g., a vacuum source). In the depicted embodiment, for example, at least one port or fitting 34 is in fluid communication with lumen 30 (and openings 38, as described below), such that fluids can be communicated between fittings 34 and a body cavity of a patient through intraluminal tube 10a.

In the embodiment shown, distal portion 22 of elongated tube 14 defines one or more openings 38 in fluid communication with lumen 30. In embodiments with more than one opening 38 (e.g., intraluminal tube 10a), the openings can be defined by distal portion 22 of elongated tube 14 in co-planar sets (sets of two or more openings, each of which is intersected by a plane that is transverse to the tube). For example, in this embodiment, a plane 42 perpendicular to elongated tube 14 and intersecting a center of an opening 38 also intersects a center of at least one other opening 38 to define a co-planar set of openings. In the depicted embodiment, the sets of openings 38 are spaced at equidistant intervals 46 to facilitate adequate fluid communication (e.g., suction) through intraluminal tube 10a (e.g., by having at least two openings 38 at each fluid communicating position along elongated tube 14). However, elongated tubes (e.g., 14) of the present intraluminal tubes can comprise any suitable number of openings 38 and/or sets of openings 38, such as, for example, 1, 2, 3, 4, 5, 6, 7, 8, 9, 10, 12, 14, 18, 20, or more openings, and the openings need not be similarly shaped, sized, and/or may possess any suitable configuration and/or placement (e.g., in part due to occlusion prevention function provided by plurality of deployable tines 62).

In the embodiment shown, sidewall 26 of distal portion 22 defines a plurality of longitudinal grooves 50. As shown, longitudinal grooves 50 extend along a majority of the length of elongated tube 14 from distal portion 22 to proximal portion 18 (e.g., such that the elongated tube may be manufactured at least in-part by extrusion). In this embodiment, each of the one or more openings 38 is disposed within one of longitudinal grooves 50. In such embodiments, for example, longitudinal grooves 50 can assist with mitigating occlusion of the openings (e.g., during suction), such as, for example, due to the recessed nature of the outer surface through which openings 38 are defined, as shown in FIG. 3.

In the embodiment shown, distal portion 22 has a transverse dimension 54 and a tip 58, and a distance 60 between the tip and the most-proximal opening 38 (e.g., or set of openings) that is furthest from the tip is between 7 to 20 times the transverse dimension of the distal portion. In other embodiments, distance 60 can be any suitable distance, such as, for example, 2, 3, 4, 5, 6, 7, 8, 9, 10, 11, 12, 13, 14, 15, 16, 17, 18, 19, 20 or more times transverse dimension 54 of distal portion 22. In such embodiments, the present intraluminal tubes (e.g., elongated tubes) can be configured to have a slim profile (e.g., a high aspect ratio, relative to some existing intraluminal tubes) while providing for proper operation (e.g., adequate suction). For example, in the embodiment shown, proper operation of slim-profile intraluminal tube 10a can be permitted and/or facilitated through occlusion prevention provided by plurality of deployable tines 62 (e.g., intraluminal tube 10a, in part through occlusion prevention features, can be configured to have a slim profile while minimizing the risk of intraluminal tube occlusion).

In the embodiment shown, intraluminal tube 10a comprises a plurality of deployable tines 62, each coupled to elongated tube 14 and disposed outside sidewall 26 of distal portion 22. As shown, intraluminal tube 10a comprises four (4) deployable tines 62; however, in other embodiments, the present intraluminal tubes can comprise any suitable number of tines, such as, for example, 1, 2, 3, 4, 5, 6, 7, 8, 9, 10, or more tines. In the embodiment shown, deployable tines 62 comprise a (e.g., flexible and/or resilient) composite material (e.g., a plastic and/or polymer, whether natural and/or synthetic), however, in other embodiments, the tines can comprise any suitable material, such as, for example, metals, such as aluminum, stainless steel, and/or the like. Such flexible and/or resilient tines 62 can facilitate patient comfort (e.g., when disposed within an internal cavity of a patient). As shown, deployable tines 62 are thin, having a length 66 much longer than (e.g., between 25 and 50 times) a maximum transverse dimension 70. In this embodiment, the tines are disposed at equiangular spaces 72 around the circumference of distal portion 22 of elongated tube 14 (as shown in FIG. 3). In some embodiments, such equiangular spacing may maximize occlusion prevention (e.g., by substantially surrounding elongated tube 14).

In this embodiment, each tine 62 is movable from a collapsed state (e.g., as shown in FIG. 2B) to a deployed state (e.g., as shown in FIG. 2A), in which a portion (e.g., 74) of the tine extends laterally away from distal portion 22 of elongated tube 14. In this embodiment, in the collapsed state, a majority of each tine lies adjacent to the distal portion of the tube (e.g., in a different one of longitudinal grooves 50, as shown in FIG. 2B). In such embodiments, intraluminal tube 10a can present a small cross-section during insertion (e.g., when collapsed, at least a majority (up to and including all) of each tine can lie within a cross-sectional perimeter of elongated tube 14, as shown in FIG. 3). In the embodiment shown, when the tines are in the collapsed state, the expanding portion (e.g., 74) of each tine 62 does not directly contact the expanding portion of any other tine (e.g., in the collapsed state, due in part to longitudinal grooves 50, a portion of elongated tube 14 lies between the expanding portions of adjacent tines, as shown in FIG. 3).

In the embodiment shown, when tines 62 are in the deployed state, the portion (e.g., 74) of each tine that extends laterally away from the distal portion of the tube (e.g., excluding ends 78 and 82, which in this embodiment are directly coupled to elongated tube 14) does not directly contact the portion of any other tine that extends laterally away from the distal portion of the tube (e.g., such that, when the tines are deployed, intraluminal tube 10*a* resembles a whisk). In other embodiments, tines 62 can be twisted and/or interwoven with one another (e.g., to form a mesh-like structure).

Tines 62 of intraluminal tube 10*a* are configured to prevent occlusion of one or more openings 38 during operation of the intraluminal tube (e.g., during suction). For example, contents of an internal cavity of a patient (e.g., stomach contents) and/or walls and/or other features of the internal cavity itself (e.g., a stomach's mucosa) could otherwise occlude openings 38. In such embodiments, intraluminal tube 10*a* is configured to increase the likelihood of continued proper function (e.g., while applying negative pressure to, for example, a patient's stomach), which may reduce the need to cease operation and/or manipulate the intraluminal tube during treatment (e.g., to relieve occlusions). Additionally, through continued proper function, intraluminal tube 10*a* can be used to obtain accurate measurements of fluids removed from the internal cavity (e.g., over a time period).

In the embodiment shown, deployment of each tine is achieved at least in part through displacement of one end of each tine (e.g., proximal end 78) relative to an opposite end (e.g., distal end 82) of the tine along tube 14. In the depicted embodiment, for example, each tine 62 comprises a proximal end 78 and a distal end 82, and at least one of the distal and proximal ends is coupled in substantially fixed relation to distal portion 22 of elongated tube 14 (e.g., and the distal and proximal ends of each tine are respectively coupled to or unitary with the distal and proximal ends of the others of the tines, described in more detail below). Particularly, in this embodiment, distal end 82 of each tine is coupled in substantially fixed relation to elongated tube 14. By way of example, as proximal end 78 of each tine is moved distally towards substantially fixed distal end 82 of the tine (e.g., via slidable movement of sheath 106 relative to elongated tube 14, as described below), a middle portion (e.g., 74) of the tine protrudes outwardly from the tube (FIG. 2A). By way of further example, as proximal end 78 of each tine is moved proximally away from substantially fixed distal end 82 of the tine, the tine can collapse (FIG. 2B). In other embodiments, proximal end 78 of each tine can be coupled in substantially fixed relation to elongated tube 14, and deployment of plurality of deployable tines 62 can be achieved, at least in part, by movement of distal end 82 relative to substantially fixed proximal end 78, as described below.

FIG. 4 depicts an operator-controlled actuator 86 suitable for use with the present intraluminal tubes. Actuator 86 is provided by way of example, and other embodiments can use or include any suitable actuation device and/or method that facilitates deployment of the tines. In this embodiment, actuator 86 comprises a first handle portion 90 and a second handle portion 94. As first handle portion 90 is moved (e.g., by a user's thumb) relative to second handle portion 94 (e.g., which can be held with a user's fingers), an actuating element 98 (e.g., a cable, rod, and/or the like) is displaced. In the embodiment shown, actuator 86 includes a locking device 102 (e.g., a thumb screw) configured to selectively secure first handle portion 90 relative to the second handle portion 94 (e.g., and releasably secure actuating element 98 relative to actuator 86).

In this embodiment, actuator 86 is configured to be coupled to proximal portion 18 of elongated tube 14 and to selectively deploy or collapse plurality of deployable tines 62. For example, in the depicted embodiment, actuator 86 is coupled to a sheath 106 (e.g., via actuating element 98) that surrounds at least a portion of and is slidably engaged with the tube. In this embodiment, sheath 106 extends to distal portion 22 of elongated tube 14 (e.g., tip 58, as shown) (e.g., and extends to or substantially extends to proximal portion 18 of the elongated tube). In such embodiments, sheath 106 can resist buckling and/or flexing relative to elongated tube 14 to facilitate actuation (e.g., deployment) of plurality of deployable tines 62. In the embodiment shown, at least a portion of sheath 106 is contoured to elongated tube 14 (e.g., such that any increase in cross-sectional area and/or outside perimeter of intraluminal tube 10*a* due to sheath 106 is minimized).

As shown, sheath 106 can be coupled to and/or be unitary with plurality of deployable tines 62 such that lateral movement of sheath 106 relative to elongated tube 14 causes expansion of the tines (e.g., which are substantially fixed at distal end 82). For example, in this embodiment, sheath 106 defines a plurality of longitudinal openings or slots 110, and tines 62 are defined by sheath 106 between openings or slots 110 (e.g., in this embodiment, sheath 106 is unitary with plurality of deployable tines 62).

Figure 6:
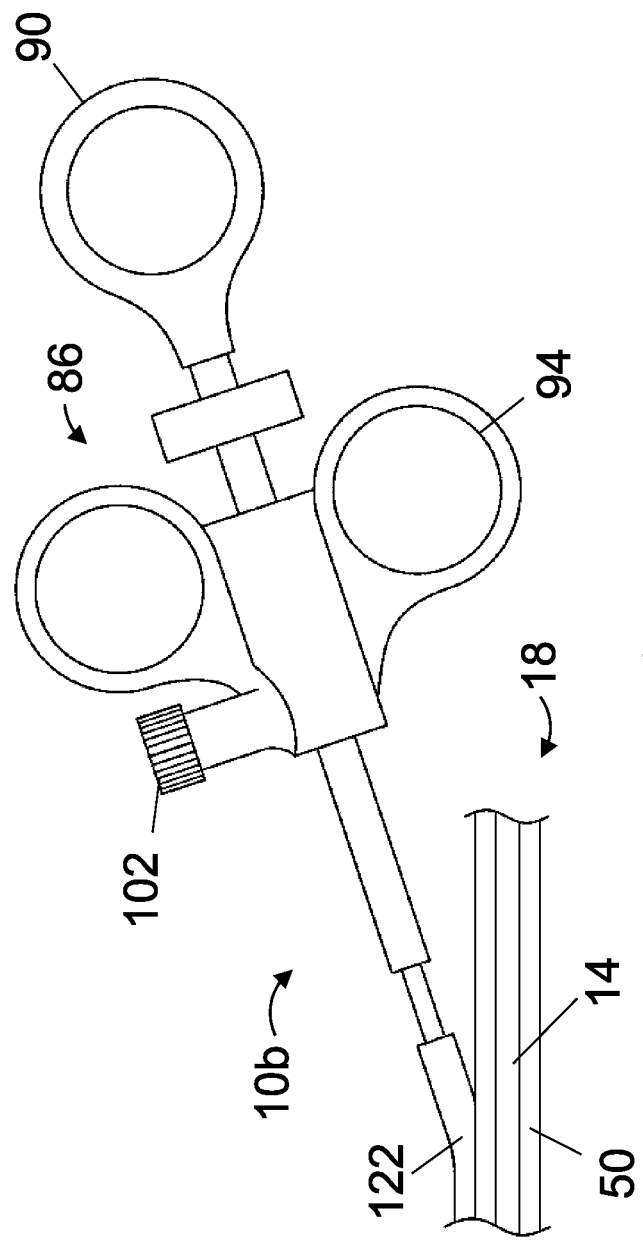
FIG. 6 is a side view of an operator-controlled actuator suitable for use with the intraluminal tube of FIG. 5A.

FIGS. 5 and 6 depict a second embodiment 10*b* of the present intraluminal tubes. Intraluminal tube 10*b* is substantially similar to intraluminal tube 10*a,* with the primary exception that intraluminal tube 10*b* comprises a flexible cable 114 coupled to tines 62 and configured to selectively deploy or collapse the tines (e.g., through coupling with operator-controlled actuator 86, as shown in FIG. 6). For example, flexible cable 114 can be coupled to a collar portion 118 which in turn is coupled to or is unitary with tines 62 such that lateral movement of collar portion 118 relative to elongated tube 14 causes the tines to expand or collapse, similarly to as described above (e.g., and collar portion 118 and/or tines 62 can resemble a truncated sheath 106). In this embodiment, collar portion 118 is coupled to or is unitary with proximal end 78 of each tine; however, in other embodiments, the collar portion can be coupled to or be unitary with distal portion 82 of the tines (e.g., and proximal end 78 of each deployable tine can be substantially fixed relative to elongated tube 14). In this embodiment, elongated tube 14 comprises a second lumen 122 and at least a portion of flexible cable 114 is (e.g., movably) disposed in the second lumen. However, in other embodiments, the flexible cable can be disposed within lumen 30 (e.g., and second lumen 122 may be omitted).

Figure 8:
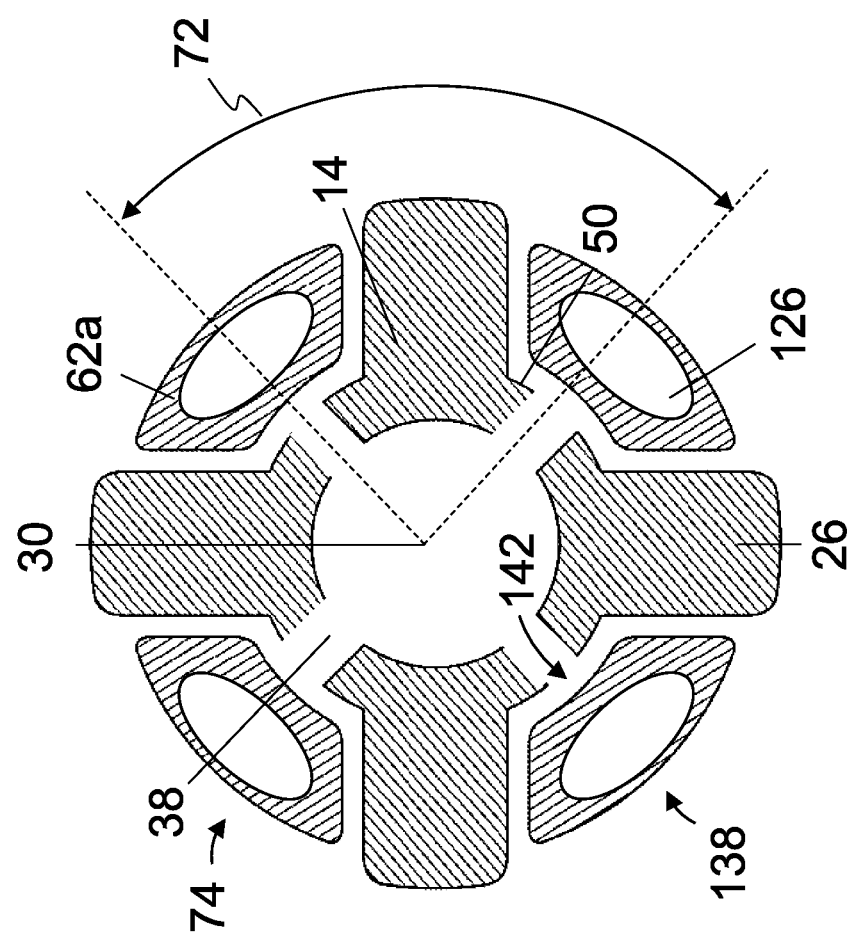
FIG. 8 is a cross-sectional end view of the intraluminal tube of FIG. 7B.

FIGS. 7A, 7B, and 8 depict a third embodiment 10*c* of the present intraluminal tubes. Intraluminal tube 10*c* is similar in many respects to intraluminal tubes 10*a* and 10*b*, with the primary exception that tines 62*a* of intraluminal tube 10*c* are inflatable. For example, in this embodiment, each of plurality of tines 62*a* defines an interior channel 126 that can extend within the tine along a majority of (e.g., up to and including all of) a length 66 of the tine. As shown, interior channel 126 of each tine is configured to be in fluid communication with a fluid source 130, such as, for example, a pump, syringe, an operator-controlled actuator (e.g., 86), and/or the like, that can be configured to communicate any suitable fluid, such as, for example, gas (e.g., air), liquid (e.g., water), and/or the like.

In this embodiment, fluid communication between fluid source 130 and tines 62a can be achieved by a second lumen 134 of elongated tube 14 (e.g., as shown). However, in other embodiments, fluid communication between tines 62a and fluid source 130 can be achieved through any suitable structure, such as, for example, through a lumen of a sheath (e.g., that can be substantially similar to 106, shown in FIGS. 1, 2A, and 2B), and/or the like. In the embodiment shown, one or more ports or fittings 34 can be configured to be in fluid communication with tines 62a, second lumen 134, fluid source 130, and/or the like (e.g., to facilitate coupling of fluid source 130 with intraluminal tube 10c).

In the embodiment shown, fluid source 130 is configured to cause movement of tines 62a between a collapsed state (FIG. 7B) and a deployed state (FIG. 7A). For example, in this embodiment, each tine 62a is flexible such that communication of fluid into interior channel 126 can exert a pressure within the interior channel that tends to expand the tine towards a deployed state, and tines 62a are resilient such that communication of fluid out of interior channel 126 can reduce a pressure within the interior channel that tends to retract the tines towards a collapsed state. By way of further example, in this embodiment, proximal end 78 and distal end 82 of each tine 62a can be coupled in substantially fixed relation to elongated tube 14 (e.g., and thus in substantially fixed relation to one another). In such embodiments, for each tine, as a pressure is increased within interior channel 126, the tine can tend to expand (e.g., elongate) and the substantially fixed relation between the distal and proximal ends of the tine can result in a middle portion (e.g., 74) of the tine protruding away from the tube (e.g., in a buckling fashion), towards a deployed state (FIG. 7A). However, in other embodiments, the distal and/or proximal ends of tines 62a need not be substantially fixed relative to one another and/or to elongated tube 14.

For example, in some embodiments, tines 62a can be configured to be moveable from a collapsed state to a deployed state through configuration, material properties, and/or the like of the tines. For example, a first portion 138 of each tine that faces away from elongated tube 14 can be more flexible (e.g., having a smaller thickness, modulus of elasticity, and/or the like) than a second portion 142 of each tine that faces towards elongated tube 14. In such embodiments, as fluid is communicated into interior channel 126, a pressure can be exerted within the interior channel that tends to deform first portion 138 to a relatively greater degree than second portion 142, resulting in a middle portion (e.g., 74) of the tine deflecting away from elongated tube 14. In these embodiments, distal end 82 and/or proximal end 78 of each tine need not be fixed and/or substantially fixed relative to one another and/or to elongated tube 14, and can instead be configured to move relative to one another (e.g., relatively closer to one another as the tine expands, and relatively further from one another as the tine collapses).

Some of the present methods for providing access to an internal cavity of a patient (e.g., a patient's stomach, colon, bladder, heart, vein, artery, other internal cavity and/or passageway, and/or the like), comprise inserting a distal portion (e.g., 22) of an elongated tube (e.g., 14) having a sidewall (e.g., 26) defining a lumen (e.g., 30) into the internal cavity, the distal portion defining one or more openings (e.g., 38) in fluid communication with the lumen and deploying a plurality of deployable tines (e.g., 62, 62a, and/or the like) (e.g., as shown in FIGS. 2A, 5A, and 7A), the tines coupled to the tube and disposed outside the sidewall of the distal portion, such that a portion (e.g., 74) of each tine extends laterally away from the elongated tube to prevent occlusion of the one or more openings. Some methods comprise applying suction through the elongated tube. Some methods comprise collapsing the tines (e.g., as shown in FIGS. 2B, 5B, and 7B) such that a majority of each tine lies adjacent the sidewall of the distal portion and removing the distal portion of the elongated tube from the internal cavity. Some methods comprise actuating an operator-controlled actuator (e.g., 86) coupled to a proximal portion of the elongated tube and configured to control deployment of the tines.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the methods and systems are not intended to be limited to the particular forms disclosed. Rather, they include all modifications and alternatives falling within the scope of the claims, and embodiments other than the one shown may include some or all of the features of the depicted embodiment. For example, elements may be omitted or combined as a unitary structure, and/or connections may be substituted. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. An intraluminal tube comprising:
a flexible, elongated tube having a proximal portion, a distal portion configured to be disposed inside of an internal cavity of a patient, and a sidewall defining a lumen extending from the proximal portion to the distal portion, the distal portion defining a plurality of openings that are spaced longitudinally and/or circumferentially from one another along the distal portion and are in fluid communication with the lumen; and
a plurality of deployable tines, each coupled to the elongated tube and disposed outside the sidewall of the distal portion, where:
 each of the plurality of deployable tines is moveable from a collapsed state to a deployed state in which a portion of the deployable tine extends laterally away from the distal portion of the elongated tube; and
 deployment of each of the plurality of deployable tines is achieved at least in part through displacement of one end of the deployable tine relative to an opposite end of the deployable tine in a direction along the elongated tube; and a flexible cable coupled to the plurality of deployable tines and configured to selectively deploy or collapse the plurality of deployable tines, at least a portion of the flexible cable movably disposed in the elongated tube.

2. The intraluminal tube of claim 1, where the sidewall of the distal portion defines a plurality of longitudinal grooves, and the plurality of deployable tines are each disposed in a different one of the plurality of the longitudinal grooves when the plurality of deployable tines are in the collapsed state.

3. The intraluminal tube of claim 2, where the plurality of openings are disposed in the plurality of longitudinal grooves.

4. The intraluminal tube of claim 1, where:
the portion of the flexible cable that is movably disposed in the elongated tube is disposed in the lumen; or
the elongated tube comprises a second lumen, and the portion of the flexible cable that is movably disposed in the elongated tube is disposed in the second lumen.

5. The intraluminal tube of claim 1, where a majority of each of the plurality of deployable tines lies adjacent to the distal portion of the elongated tube when in the collapsed state.

6. The intraluminal tube of claim 1, where the portion of each of the plurality of deployable tines that extends laterally away from the distal portion of the elongated tube does not directly contact the portion of any other of the plurality of deployable tines that extends laterally away from the distal portion of the elongated tube when in the deployed state.

7. The intraluminal tube of claim 1, where the distal portion comprises a transverse dimension and a tip, and a distance between the tip and a most-proximal one of the plurality of openings furthest from the tip is between 7 and 20 times the transverse dimension of the distal portion.

8. The intraluminal tube of claim 1, where each of the plurality of deployable tines lies substantially within a cross-sectional perimeter of the elongated tube when in the collapsed state.

9. The intraluminal tube of claim 1, where each of the deployable tines has:
an outer surface; and
a cross-section, taken perpendicularly to a length of the deployable tine, that has a convex portion defined by the outer surface.

10. An intraluminal tube comprising:
a flexible, elongated tube having a proximal portion, a distal portion configured to be disposed inside of an internal cavity of a patient, and a sidewall defining a lumen extending from the proximal portion to the distal portion, the distal portion defining a plurality of openings that are spaced longitudinally and/or circumferentially from one another along the distal portion and are in fluid communication with the lumen; and
a plurality of deployable tines, each coupled to the elongated tube and disposed outside the sidewall of the distal portion;
where each of the plurality of deployable tines:
is moveable from a collapsed state to a deployed state in which a portion of the deployable tine extends laterally away from the distal portion of the elongated tube; and
comprises a distal end and a proximal end, the distal end being coupled in fixed relation to the distal portion of the elongated tube, and the proximal end being disposed closer to the distal portion of the elongated tube than to the proximal portion of the elongated tube when the deployable tine is in the collapsed state; and where the sidewall of the distal portion defines a plurality of longitudinal grooves, the plurality of openings being disposed in the plurality of longitudinal grooves, and the plurality of deployable tines are each disposed in a different one of the plurality of longitudinal grooves when the plurality of deployable tines are in the collapsed state.

11. The intraluminal tube of claim 10, where deployment of each of the plurality of deployable tines is achieved at least in part through displacement of the proximal end of the deployable tine relative to the distal end of the deployable tine in a direction along the elongated tube.

12. The intraluminal tube of claim 10, where:
a distance between the portion of the deployable tine and the distal portion of the elongated tube increases as the portion of the deployable tine extends laterally away from the distal portion of the elongated tube; and
the plurality of deployable tines each define an interior channel configured to be in fluid communication with a fluid source, the fluid source configured to cause movement of the deployable tine between the collapsed state and the deployed state.

13. The intraluminal tube of claim 12, where the elongated tube comprises a second lumen configured to communicate fluid between the fluid source and the interior channel of each of the plurality of deployable tines.

14. The intraluminal tube of claim 10, comprising a flexible cable coupled to the plurality of deployable tines and configured to selectively deploy or collapse the plurality of deployable tines, at least a portion of the flexible cable movably disposed in the elongated tube.

15. The intraluminal tube of claim 10, where the portion of each of the plurality of deployable tines that extends laterally away from the distal portion of the elongated tube does not directly contact the portion of any other of the plurality of deployable tines that extends laterally away from the distal portion of the elongated tube when in the deployed state.

16. The intraluminal tube of claim 10, where each of the plurality of deployable tines lies substantially within a cross-sectional perimeter of the elongated tube when in the collapsed state.

17. The intraluminal tube of claim 10, where each of the deployable tines has:
an outer surface; and
a cross-section, taken perpendicularly to a length of the deployable tine, that has a convex portion defined by the outer surface.

18. A method for providing access to an internal cavity of a patient comprising:
inserting a distal portion of a flexible, elongated tube having a sidewall defining a lumen into the internal cavity, the distal portion defining a plurality of openings that are:
spaced longitudinally and/or circumferentially from one another along the distal portion; and
in fluid communication with the lumen;
deploying a plurality of deployable tines, the plurality of deployable tines coupled to the elongated tube such that a distal end of each of the deployable tines is coupled to the distal portion of the elongated tube, a proximal end of each of the deployable tines is attached to a sheath that surrounds at least a section of the distal portion of the elongated tube and is disposed closer to the distal portion of the elongated tube than to a proximal portion of the elongated tube, and the plurality of deployable tines are disposed outside the sidewall of the distal portion, the deploying is such that a portion of each of the plurality of deployable tines extends laterally away from the elongated tube to prevent occlusion of the plurality of openings; and applying suction through the elongated tube.

* * * * *